United States Patent
Vilsmeier

(10) Patent No.: US 7,194,295 B2
(45) Date of Patent: Mar. 20, 2007

(54) MEDICAL NAVIGATION AND/OR PRE-OPERATIVE TREATMENT PLANNING WITH THE ASSISTANCE OF GENERIC PATIENT DATA

(75) Inventor: Stefan Vilsmeier, Kufstein (AT)

(73) Assignee: BrainLAB AG, Feldkirchen (DE)

( * ) Notice: Subject to any disclaimer, the term of this patent is extended or adjusted under 35 U.S.C. 154(b) by 654 days.

(21) Appl. No.: 10/133,867

(22) Filed: Apr. 26, 2002

(65) Prior Publication Data

US 2003/0185346 A1 Oct. 2, 2003

(30) Foreign Application Priority Data

Mar. 27, 2002 (EP) .................................. 02007218

(51) Int. Cl.
*A61B 5/00* (2006.01)
(52) U.S. Cl. ...................... 600/416; 600/407; 600/425; 128/898; 382/128; 382/154; 382/173; 382/190
(58) Field of Classification Search ........ 600/407–482; 128/898; 382/128, 154, 173, 190
See application file for complete search history.

(56) References Cited

U.S. PATENT DOCUMENTS

| | | | |
|---|---|---|---|
| 5,806,518 A | * | 9/1998 | Mittelstadt .................. 600/407 |
| 5,891,034 A | * | 4/1999 | Bucholz ...................... 600/426 |
| 6,021,343 A | * | 2/2000 | Foley et al. ................. 600/429 |
| 6,033,415 A | | 3/2000 | Mittelstadt et al. |
| 6,711,432 B1 | * | 3/2004 | Krause et al. ............... 600/427 |

FOREIGN PATENT DOCUMENTS

| | | |
|---|---|---|
| DE | 100 37 491 | 2/2002 |
| EP | 1222636 | 7/2002 |
| WO | 99/59106 | 11/1999 |
| WO | 01/22368 | 3/2001 |

\* cited by examiner

*Primary Examiner*—Brian L. Casler
*Assistant Examiner*—William Jung
(74) *Attorney, Agent, or Firm*—Renner, Otto, Boisselle & Sklar, LLP

(57) ABSTRACT

The invention relates to a method for computer-assisted medical navigation and/or pre-operative treatment planning, wherein the current position of a patient or a part of a patient's body and the positions of medical treatment devices or treatment-assisting devices are detected by means of a position detection unit, and wherein said detected positional data are assigned to body structure data, in order to jointly use said body structure data in assignment with said positional data, within the context of assisting the treatment, wherein body structure data are used which are obtained based on a generic model which has been adapted by linking it with patient-characteristic detection data.

16 Claims, No Drawings

MEDICAL NAVIGATION AND/OR PRE-OPERATIVE TREATMENT PLANNING WITH THE ASSISTANCE OF GENERIC PATIENT DATA

The present invention relates to a method for computer-assisted medical navigation and/or pre-operative treatment planning. In general terms, the current position of a patient or a part of a patient's body and the positions of medical treatment devices or treatment-assisting devices are detected in such navigation methods by means of a position detection unit, and the detected positional data are assigned to body structure data, in order to jointly use the body structure data in assignment with the positional data, within the context of assisting the treatment. Such a navigation system is described for example in DE 196 39 615 C2.

Computer-assisted, stereotactic systems which work with the aid of body structure data obtained from tomographic detection systems and with the assistance of x-ray images produced in situ are known for example from U.S. Pat. No. 4,791,934 and U.S. Pat. No. 5,799,055. X-ray imaging used to assist in operations is furthermore discussed in U.S. Pat. Nos.: 5,967,982; 5,772,594; and 5,784,431.

Where accurate medical navigation is to be provided, the prior art still works with the aid of body structure data originating for example from tomographic detection systems such as for example computer tomography devices or nuclear spin tomography devices. The patient to be treated is thus positionally registered in situ with respect to the image data determined beforehand, and operating instruments are then virtually displayed in the same relation to the image data as to the actual patient, to make the body structure data or if possible also x-ray image data useful to the surgeon in the operating room.

The disadvantage of such methods, in which tomographs (CT, MR) or x-ray images are produced especially for navigating within the framework of treatment, is on the one hand the radiation load on the patient which thus arises, and on the other hand the high costs, since such devices are very expensive both to purchase and to maintain and operate.

Attempts have been made to develop systems which may be employed without body structure data separately detected beforehand, for example based on statistical models of image data sets for body structures. However, such systems lack the required accuracy for the respective patient to be treated.

It is the object of the present invention to provide a method for computer-assisted medical navigation and/or pre-operative treatment planning which overcomes the disadvantages of the prior art described above. In particular, it is intended to avoid producing a separate image data set—which is cost-intensive and a burden to health—for navigation/treatment planning, while nonetheless providing sufficiently accurate navigation.

This object is solved in accordance with the invention by using body structure data in computer-assisted medical navigation method and/or treatment planning method, said body structure data being obtained based on a generic model which has been adapted by linking it with patient-characteristic detection data.

When "navigation" is mentioned in the following, this term is intended in principle to also include pre-operative treatment planning in the context of which a surgeon determines an ideal approach for a treatment beforehand, i.e. for example, manually determines and fixes the ideal position of an implant.

The advantages of the present invention are based on the fact that using a generic model adapted to the patient, it is no longer necessary to produce a separate data set for the body structure, for the treatment for which medical navigation is to be provided. On the one hand, this spares the patient the radiation load, and the costs of producing the data set (for example by tomography) can be saved, while on the other hand, linking the generic body structure data with patient-characteristic detection data provides a data set which enables highly accurate medical navigation. The generic model, which can be a kind of universal model for the body structure in question, for which all the relevant data are available, does not include data tailored specifically to the patient in question, but does include sufficient anatomical and/or body structure data to be able to provide a sufficiently accurate basis for medical navigation, once it has been adapted with the aid of patient-characteristic detection data.

The invention as it has been described above is defined by patent claim 1. The sub-claims define preferred embodiments of the invention, such as are also discussed more specifically in the following.

It is possible within the framework of the present invention to provide the body structure data in the form of an image data set, in particular as a tomographic imaging data set.

In this way, separate image detection data sets are nor generated, as in methods in accordance with the prior art, rather the generic model itself is already provided in the form of an image data set which can then be adapted to the respective patient, to obtain an image data set which is valid for the patient. This image data set can then be employed just like one produced cost-intensively and with pre-operative radiation load for the patient. It is conceivable, for example, to use a generic model comprising a typical or average body structure, for example a simple, model representation of a vertebra or of a bone/body structure.

The generic model can also include a statistical model of the body structure, in particular based on statistical evaluations of an indefinite number of image data sets, for example of actual vertebra image data sets.

Furthermore, the possibility exists of providing the generic model directly as a kind of model package for a multitude of body structures of the same type. In this case, it is possible when adapting the model to isolate from the multitude of models in the package the one which best matches the patient-characteristic detection data, such that the model only has to be slightly adapted with computer assistance.

Within the framework of the present invention, the generic model can comprise a two- or three-dimensional data set of a body structure, in particular also a geometric model. In other words;, the generic model can consist both of three-dimensional data (for example, a vertebra model) and two-dimensional data (for example, virtual x-ray images) or also of a model in the form of geometric data. These data can, for example, be angles and/or trajectory information which can be displayed for the physician and for example indicate to him the ideal position of an implant.

Various types of patient-characteristic data are outlined in the following, such as can be used for adapting the generic model. It is also always possible to employ combinations of such data, referred to as diagnostic data in the following, to this end.

The patient-characteristic data can be x-ray data, from x-ray images produced before or during treatment, in particular bi-planar or multi-planar x-ray images. An example of this is when x-ray images of the patient are already available which were produced within the context of previous examinations. Data about body structures from these "old" x-ray images are particularly suitable if deviations of form with respect to the generic model are to be calculated in.

It is, however, also possible even during treatment to produce individual x-ray images of the patient and to include this information in adapting the generic model. The advantage as compared to convention "x-ray navigation" is then that it is not necessary to produce a large multitude of x-ray images, such as are used in navigation based on x-ray images; it is sufficient for adapting the generic model to produce just one or very few x-ray images, which moreover can be restricted to a very small section of the body. This significantly reduces the radiation load as compared to conventional x-ray navigation.

The above applies in the same way to computer tomography or nuclear spin tomography image data. Data may be used which derive from tomographic images produced much earlier, but whose information is sufficient for suitably adapting the generic model.

Moreover, the diagnostic image data can also be digitally reconstructed x-ray image data (DRRs=digitally reconstructed radiographs) which can for example be produced from tomographic image data sets already available, without the patient again having to be subjected to x-ray imaging.

It is, however, not absolutely necessary to use complicated, patient-characteristic detection data and/or diagnostic data in this way, to be able to adapt the generic model sufficiently. It can be perfectly sufficient to use acquired point-positional information of the patient's body structure, in particular of natural or artificial landmarks. The patient-characteristic diagnostic data can then, for example, be just the distance between two landmarks (for example, apophyses), which alone can give sufficient information about how the generic model should be restructured. Similarly, data on size, weight or lengths of the body section or of one or more limbs of the patient can be used as a basis for this.

The generic model can be adapted within the context of the invention using one or more of the following methods:
  manually adapting with the assistance of image representation, in particular by offsetting points and landmarks or by shifting, rotating, stretching or compressing the generic model on a screen output by means of user-interface means;
  automatic image fusion methods, in particular based on automatically identifying particular anatomical features;
  registering and/or fusing image data of the generic model, in particular digitally reconstructed x-ray images, and the same from computer tomography or nuclear spin tomography image data sets.

The generic model can thus be fused using diagnostic methods either automatically, for example by automatically identifying particular anatomical features critical for fusion, or manually, for example by shifting, rotating, stretching etc. When the generic model is fused with actual patient information by acquiring an indefinite quantity of point information on the patient (landmarks), it is possible to use a so-called surface-matching method, i.e. a computer-assisted image adapting method, to fuse the image data. From the various methods described above, capturing the diagnostic data and adapting the generic model are combined in accordance with an embodiment of the invention, such that alongside the diagnostic data (for example, x-ray images acquired intra-operatively), additional points on the patient are also recorded, in the form of landmarks or randomly acquired points, and used to detect and adjust the position of the model or its form even more accurately, so as to enable more accurate navigation.

A hip-thigh arrangement (pelvis/femur) can also be registered by means of registered x-ray images and a generic model. The hip could then be registered for example by assigning landmarks between the generic model and one or more x-ray images (fluoroscopy, for example at an angle of 30°) by mathematical coupling.

Generally speaking, the positional data in the method in accordance with the invention, obtained while determining the patient-characteristic detection data, in particular by acquiring landmark; positions or by x-ray imaging registered in the navigation system, can be used to register the adapted body structure data in the navigation system and to visually display or introduce treatment devices and/or treatment-assisting devices in their registration to the adapted body structure. In other words, the step of capturing the diagnostic data is also simultaneously used in this way to register the patient and the adapted generic model for navigation. As long as the data of the model are fused with registered data, i.e. data which are clearly determined in the spatial position, for example registered fluoroscopy images of an x-ray navigation software, or the data of the model are registered with landmarks, or a combination of the two methods, these can be used for computer-assisted surgery and for example for minimally invasive operations in which instruments or implants are displayed in relation to a fused model.

The method in accordance with the present invention can be used both to assist in surgery in which the surgeon is provided with navigating aids on screens, and within the context of radiotherapy and/or radiosurgery. Navigation can be based on optical tracking or on magnetic tracking.

The present invention further comprises a program which, when running on a computer or loaded on a computer, causes the computer to perform one or more of the methods described above, and a computer program storage medium comprising such a program.

In summary, it remains to be established with respect to the above invention that it eliminates or at least minimizes the radiation load and the costs of tomographic imaging methods, and that it also has the advantage as compared to pure x-ray navigation that it enables the surgeon three-dimensional navigation and orientation. Further advantages lie in the fact that the steps resulting in the patient being registered are substantially less complicated and that the method in accordance with the invention can result in the patient being registered using few manual steps. Costly diagnostic examinations are simplified, and acquiring points/landmarks on the patient for registering can also for example be made superfluous, if already calibrated data (for example, registered x-ray data) are used and additional useful information is obtained through fusion with the generic model (for example, converting a quantity of two-dimensional information into actual three-dimensional information).

It is thus possible in accordance with the invention to automatically display the ideal position of implants or instruments at little cost, such that surgery can be performed more quickly, more securely, and less invasively.

The invention claimed is:

1. A method for computer-assisted medical navigation and/or pre-operative treatment planning, comprising:
  linking a generic model with patient-characteristic data to obtain body structure data;

detecting a current position of a patient or a part of a patient's body and positions of medical treatment devices or treatment-assisting devices by a position detection unit, wherein said detected positional data are assigned to the body structure data in order to jointly use said body structure data in assignment with said positional data within the context of assisting the treatment;

obtaining additional points on the patient in the form of landmarks or randomly acquired points; and using the additional points to further correlate the body structure data to the patient or part of the patient's body.

2. The method as set forth in claim 1, wherein said body structure data are provided in the form of image data.

3. The method as set forth in claim 2, wherein the image data set is a tomographic image data set.

4. The method as set forth in claim 1, wherein said generic model comprises a typical or average body structure.

5. The method as set forth in claim 1, wherein said generic model includes a statistical model of said body structure.

6. The method as set forth in claim 5, wherein the statistical model is based on statistical evaluations of a number of image data sets of the body structure.

7. The method as set forth in claim 1, wherein said generic model includes a multitude of body structures of the same type.

8. The method as set forth in claim 1, wherein said generic model comprises a two- or three-dimensional data set of a body structure, and/or a geometric model.

9. The method as set forth in claim 1, wherein said positional data obtained while determining said patient-characteristic data can be used to register said adapted body structure data in said navigation system and to visually display or use treatment devices and/or treatment-assisting devices in their registration to said adapted body structure.

10. The method as set forth in claim 9, wherein said patient-characteristic detection data includes acquiring landmark positions or x-ray imaging registered in said navigation system.

11. The method as set forth in claim 1, wherein the generic model is based on data corresponding to a weight of the patient or the part of the patient's body.

12. The method as set forth in claim 1, wherein linking includes surface matching the generic model to the patient-characteristic data.

13. A method for computer-assisted medical navigation and/or pre-operative treatment planning, comprising:

detecting a current position of a patient or a part of a patient's body and positions of medical treatment devices or treatment-assisting devices by a position detection unit, wherein said detected positional data are assigned to body structure data in order to jointly use said body structure data in assignment with said positional data within the context of assisting the treatment, and wherein said body structure data are obtained based on a generic model which has been adapted by linking the generic model with patient-characteristic detection data, wherein said patient-characteristic data are diagnostic data obtained from the patient, said diagnostic data obtained from at least one of the following, alone or in combination:

x-ray image data from x-ray images produced before or during treatment;

bi-planar or multi-planar x-ray images;

computer tomography or nuclear spin tomography image data;

digitally reconstructed x-ray image data (DRRs=digitally reconstructed radiographs);

acquired point-positional information of the patient's body structure using natural or artificial landmarks;

data on size, weight or lengths of the body section or one or more limbs of the patient.

14. A method for computer-assisted medical navigation and/or pre-operative treatment planning, comprising:

detecting a current position of a patient or a part of a patient's body and positions of medical treatment devices or treatment-assisting devices by a position detection unit, wherein said detected positional data are assigned to body structure data in order to jointly use said body structure data in assignment with said positional data within the context of assisting the treatment, and wherein said body structure data are obtained based on a generic model which has been adapted by linking the generic model with patient-characteristic detection data, wherein said generic model can be adapted using one or more of the following methods:

manually adapting with the assistance of image representation;

automatic image fusion methods based on automatically identifying particular anatomical features; and registering and/or fusing image data of said generic model digitally reconstructed x-ray images, and the same from computer tomography or nuclear spin tomography image data sets, after which the adapted body structure data are calculated by computer-assistance.

15. The method as set forth in claim 14, wherein manually adapting with the assistance of image representation includes offsetting points and landmarks or by shifting, rotating, stretching or compressing said generic model on a screen output by means of user-interface means.

16. A computer program embodied on a computer readable medium for computer-assisted medical navigation and/or pre-operative treatment planning, comprising:

code that links a generic model with patient-characteristic data to obtain body structure data;

code that detects a current position of a patient or a part of a patient's body and positions of medical treatment devices or treatment-assisting devices by a position detection unit, wherein said detected positional data are assigned to the body structure data in order to jointly use said body structure data in assignment with said positional data within the context of assisting the treatment;

code that obtains additional points on the patient in the form of landmarks or randomly acquired points; and code that uses the additional points to further correlate the body structure data to the patient or part of the patient's body.

* * * * *